United States Patent [19]

Ito et al.

[11] Patent Number: 5,859,026
[45] Date of Patent: Jan. 12, 1999

[54] QUINOLINE CARBOXYLIC ACID

[75] Inventors: Yasuo Ito; Hideo Kato; Shingo Yasuda; Noriyuki Kada; Toshihiko Yoshida, all of Fukui; Yoichi Yamamoto, Ishikawa, all of Japan

[73] Assignee: Hokuriku Seiyaku Co., Ltd., Fukui, Japan

[21] Appl. No.: 860,469

[22] PCT Filed: Dec. 20, 1995

[86] PCT No.: PCT/JP95/02614

§ 371 Date: Jul. 9, 1997

§ 102(e) Date: Jul. 9, 1997

[87] PCT Pub. No.: WO96/22988

PCT Pub. Date: Aug. 1, 1996

[30] Foreign Application Priority Data

Jan. 24, 1995 [JP] Japan ..................................... 7/27270

[51] Int. Cl.⁶ ....................... A61K 31/47; C07D 215/233
[52] U.S. Cl. .......................................... 514/312; 546/153
[58] Field of Search .............................. 546/153; 514/312

[56] References Cited

U.S. PATENT DOCUMENTS

| 4,665,079 | 5/1987 | Culbertson et al. | 514/312 |
|---|---|---|---|
| 4,753,953 | 6/1988 | Masuzawa et al. | 514/312 |
| 4,771,055 | 9/1988 | Domagala et al. | 514/312 |
| 4,791,118 | 12/1988 | Masuzawa et al. | 514/312 |
| 4,886,810 | 12/1989 | Matsumoto et al. | 514/312 |
| 4,894,458 | 1/1990 | Masuzawa et al. | 540/575 |
| 4,990,517 | 2/1991 | Petersen et al. | 514/300 |
| 5,043,450 | 8/1991 | Masuzawa et al. | 546/156 |
| 5,057,520 | 10/1991 | Chu et al. | 514/300 |
| 5,057,523 | 10/1991 | Chu et al. | 514/312 |
| 5,137,892 | 8/1992 | Chu et al. | 514/278 |
| 5,173,484 | 12/1992 | Petersen et al. | 514/187 |
| 5,190,955 | 3/1993 | Schriewer et al. | 514/312 |
| 5,284,842 | 2/1994 | Petersen et al. | 514/187 |
| 5,286,723 | 2/1994 | Hayakawa et al. | 514/213 |
| 5,322,942 | 6/1994 | Rapoport et al. | 544/297 |
| 5,547,962 | 8/1996 | Ito et al. | 514/312 |

FOREIGN PATENT DOCUMENTS

| 0 237955 | 9/1987 | European Pat. Off. . |
|---|---|---|
| 0284935 | 10/1988 | European Pat. Off. . |
| 0360258 | 3/1990 | European Pat. Off. . |
| 0 391169 | 10/1990 | European Pat. Off. . |
| 0 641793 | 3/1995 | European Pat. Off. . |
| 62-215572 | 9/1987 | Japan . |
| 2-158855 | of 1988 | Japan . |
| 63-152318 | 6/1988 | Japan . |
| 63-258855 | 10/1988 | Japan . |
| 63-275567 | 11/1988 | Japan . |
| 2-19377 | of 1990 | Japan . |
| 2-19380 | of 1990 | Japan . |
| 2-19377 | 1/1990 | Japan . |
| 2-142786 | 5/1990 | Japan . |
| 2-290870 | 11/1990 | Japan . |
| 6-215213 | of 1994 | Japan . |
| 6-508136 | of 1994 | Japan . |
| 7-309864 | 11/1995 | Japan . |
| 212805 | 1/1989 | New Zealand . |
| 92-10492 | 6/1992 | WIPO . |
| 92/21675 | 12/1992 | WIPO . |
| 93-3026 | 2/1993 | WIPO . |

OTHER PUBLICATIONS

English Language Derwent Abstract No. 88–216579, 1988.
English Language Derwent Abstract No. 90–064630, 1990.
The Merck Index, 11th Edition, No. 2315, 1989.
*Quinoline Antimicrobial Agents*, 2nd Edition, chapter 26, "Adverse Effects" Edited by D.C. Hooper and J.S. Wolfson, American Society for Microbiology, Washington, DC, 1993, pp. 489–512.
Mutagenicity Test (Henigen–sei Shiken) 2(3), 154–161 (1993).
Environmental and Molecular Mutagenesis 13:238–252 (1989).
English Language Derwent Abstract No. 88–365129.
Domagala et al., J. Med. Chem. 36, 871–882 (1993).
Hagen et al., J. Med. Chem. 37, 733–738 (1994).
International Search Report, 1991.
International Preliminary Examination Report, 1992.

*Primary Examiner*—Mukund J. Shah
*Assistant Examiner*—Pavanaram K. Sripada
*Attorney, Agent, or Firm*—Greenblum & Bernstein, P.L.C.

[57] ABSTRACT

5-Amino-7-((3S,4S)-3-amino-4-methyl (or ethyl)-1-pyrrolidinyl)-1-cyclopropyl-6-fluoro-1,4-dihydro-8-methyl-4-oxoquinoline-3-carboxylic acid or a pharmacologically acceptable salt thereof represented by the following formula wherein asymmetric carbon atoms marked with asterisks are in the S-configurations and $R^1$ represents methyl group or ethyl group; and an antibacterial agent comprising said compound as an active ingredient.

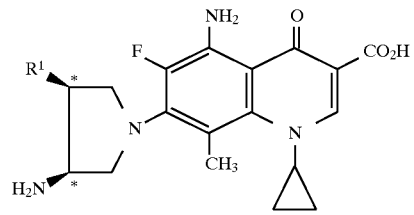

6 Claims, No Drawings

QUINOLINE CARBOXYLIC ACID

FIELD OF THE INVENTION

The present invention relates to 5-amino-8-methyl-7-pyrrolidinylquinoline-3-carboxylic acid derivatives and pharmacologically acceptable salts thereof which are useful for active ingredients of antibacterial agents, as well as to antibacterial agents comprising the substances as active ingredients.

BACKGROUND ART

Ciprofloxacin (The Merck Index 11th Edition, No.2315) is known as one of quinolone-type synthetic antibacterial agents that have cyclopropyl group at the 1-position of quinoline structure. A number of compounds with modifications at 5, 7, and 8-positions of this compound have been synthesized in order to improve antibacterial activity, physicochemical properties, e.g., water solubility, and safety of ciprofloxacin. For example, the Japanese Patent Unexamined Publication (KOKAI) No. (Sho)62-215572/1987 discloses the compound as set out below in which a piperazinyl group is introduced at the 7-position of the quinoline structure that has amino group at the 5-position and methyl group at the 8-position. However, a compound has not yet been known in which 3-amino-4-methyl (or ethyl)-pyrrolidinyl group is introduced at the 7-position of the quinoline structure having amino group at the 5-position and methyl group at the 8-position.

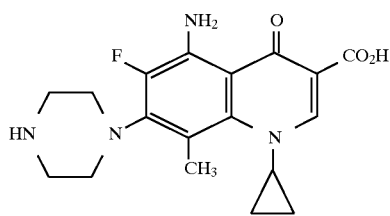

Although the quinolone-type synthetic antibacterial agents so far reported have potent antibacterial activities, they have problems from a viewpoint of safety, for example, phototoxicity, induction of chromosomal aberration, and induction of convulsion. These problems of the quinolone-type synthetic antibacterial agents are explained in each of the following literatures: Quinolone Antimicrobial Agents, 2nd edition, Chapter 26, Ed. By D. C. Hooper and J. S. Wolfson, American Society for Microbiology, Washington D.C., 1993, p.489 (phototoxicity, induction of chromosomal aberration, induction of convulsion and other); Mutagenicity Test (Henigen-sei Shiken) 2(3), p.154, 1993 (chromosomal aberration and other); and Environ. Mol. Mutagen., 13, p.238, 1989 (chromosomal aberration and other).

An object of the present invention is to provide quinolone-type synthetic antibacterial agents having high antibacterial activity, and in addition, whose adverse reactions such as phototoxicity, induction of chromosomal aberration, and induction of convulsion are reduced.

As for correlation between structures and adverse reactions of the quinolone-type synthetic antibacterial agents, the following general predictability has been noted in view of the state of the art: (A) as a substituent at the 8-position of a quinoline structure, a somewhat bulky substituent such as a chlorine atom or methyl group is preferred from a viewpoint of antibacterial activity; however, a compound having a chlorine atom at the 8-position has strong adverse reactions such as phototoxicity or induction of chromosomal aberration, and a compound having methyl group exhibits strong adverse reactions such as induction of chromosomal aberration; (B) amino group, halogen atoms, methyl group and the like have been used as a substituent at the 5-position of a quinoline structure; however, these substituents decrease antibacterial activity, or alternatively, increase adverse reactions such as phototoxicity or induction of chromosomal aberration; and (C) antibacterial activity is improved when one of 3-aminopyrrolidines is introduced as a substituent at the 7-position of a quinoline structure; however, adverse reactions such as induction of chromosomal aberration are increased.

The inventors of the present invention conducted various researches to achieve the foregoing object. As a result, they found that, contrary to the aforementioned general predictability, 1-cyclopropyl-6-fluoro-1,4-dihydro-4-oxo-quinoline-3-carboxylic acid derivatives, in which amino group at the 5-position, methyl group at the 8-position, and 3-amino-4-methyl (or ethyl)-pyrrolidinyl group at the 7-position are substituted together, have potent antibacterial activities, and that the compounds are highly safe with reduced adverse reactions such as phototoxicity, induction of chromosomal aberration, and induction of convulsion. The Japanese patent application No. (Hei) 6-215213/1994 was filed on the basis of this invention.

The inventors of the present invention conducted further researches, and they consequently found that, among compounds that fall within the compounds of the aforementioned general formula, optically active compounds each having the substituent in a specific stereostructure have both excellent antibacterial activities and remarkably high safeties. The present invention was achieved on the basis of these findings.

DISCLOSURE OF THE INVENTION

According to the first aspect of the present invention, there are provided 5-amino-7-((3S,4S)-3-amino-4-methyl-1-pyrrolidinyl)-1-cyclopropyl-6-fluoro-1,4-dihydro-8-methyl-4-oxoquinoline-3-carboxylic acid, and 5-amino-7-((3S,4S)-3-amino-4-ethyl-1-pyrrolidinyl)-1-cyclopropyl-6-fluoro-1,4-dihydro-8-methyl-4-oxoquinoline-3-carboxylic acid represented by the following formula (1) wherein the asymmetric carbon atoms marked with asterisks are in the S-configurations, and $R^1$ represents methyl group or ethyl group, and pharmacologically acceptable salts thereof. Medicaments and antibacterial agents comprising the aforementioned compounds as active ingredients are also provided.

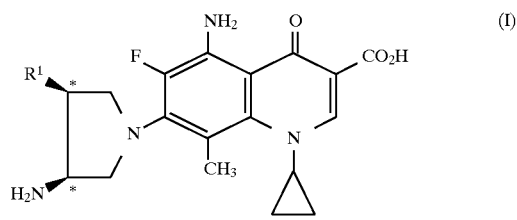

As preferred embodiments according to the invention, there are provided 5-amino-7-((3S,4S)-3-amino-4-methyl-1-pyrrolidinyl)-1-cyclopropyl-6-fluoro-1,4-dihydro-8-methyl-4-oxoquinoline-3-carboxylic acid and a pharmacologically acceptable salt thereof, and a medicament and an antibacterial agent comprising said compound as an active ingredient.

According to another aspect of the present invention, there are provided 5-amino-7-((3S,4S)-3-amino-4-methyl- 1-pyrrolidinyl)-1-cyclopropyl-6-fluoro-1,4-dihydro-8-methyl-4-oxoquinoline-3-carboxylic acid derivatives and 5-amino-7-((3S,4S)-3-amino-4-ethyl-1-pyrrolidinyl)-1-cyclopropyl-6-fluoro-1,4-dihydro-8-methyl-4-oxoquinoline-3-carboxylic acid derivatives represented by the following formula (II) wherein the asymmetric carbon atoms marked with asterisks are in the S-configurations, $R^1$ represents methyl group or ethyl group, $R^2$ represents a hydrogen atom, a lower alkyl group, or $BF_2$ group, and $R^3$ and $R^4$ independently represent a hydrogen atom or an amino protective group, with the proviso that $R^2$, $R^3$, and $R^4$ are not simultaneously hydrogen atoms. These compounds are useful as synthetic intermediates for the manufacture of the aforementioned compound (I).

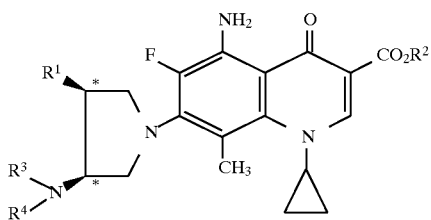

(II)

BEST MODE FOR CARRYING OUT THE INVENTION

The compounds (I) of the present invention can be converted into salts, if desired, preferably into pharmacologically acceptable salts. Further conversions into compounds in the free form may be carried out by generating bases or acids from the resulting salts. As the pharmacologically acceptable salts, acid addition salts or alkali addition salts may be used. In addition, the compounds (I) of the present invention and salts thereof that may exist in any crystalline forms, as well as any hydrates of the compound (I) of the present invention and salts thereof fall within the scope of the present invention.

As the acid addition salts, for example, mineral acid salts such as hydrochlorides, hydrobromides, nitrates, sulfates, hydroiodides, or phosphates; and organic acid salts such as acetates, maleates, fumarates, citrates, oxalates, malates, methanesulfonates, p-toluenesulfonates, mandelates, 10-camphorsulfonates, tartrates, lactates, 5-oxotetrahydrofuran-2-carboxylates, or 2-hydroxygultarates may be used. As the alkali addition salts, for example, inorganic alkali salts such as sodium salts, potassium salts, calcium salts, magnesium salts, or ammonium salts, or salts of organic bases such as ethanolamine or N,N-dialkylethanolamine may be used.

In the compounds (II) of the present invention, $R^2$ represents a hydrogen atom, a lower alkyl group, or $BF_2$. As the lower alkyl group, straight- or branched-chain alkyl groups having 1 to 6 carbon atoms, preferably 1 to 4 carbon atoms. For example, methyl group, ethyl group, n-propyl group, isopropyl group, n-butyl group, isobutyl group, sec-butyl group, or tert-butyl group may preferably be used.

As each of the amino protective groups represented by $R^3$ and $R^4$, any groups may be used so far that they are substantially inert in a reaction system in which the amino group should not be involved in the reaction, and that they can be readily cleaved under conditions of a certain deblocking reaction to regenerate the amino group. For example, lower alkanoyl groups, halogenated lower alkanoyl groups, arylcarbonyl groups, aryloxycarbonyl groups, aralkyloxycarbonyl groups, lower alkyloxycarbonyl groups, alkylsilyl groups, or aralkyl groups may be used.

Where these protective groups are used, an ordinary skilled artisan may appropriately decide, depending on the sort of the protective group used as $R^3$, which of a protective group or a hydrogen atom should be applied as $R^4$. For example, where a lower alkanoyl group is used as $R^3$, a hydrogen atom is generally used as $R^4$. Where benzyl group is used as $R^3$, an alkylsilyl group or other benzyl group can be introduced as $R^4$. Where both of $R^3$ and $R^4$ are protective groups, examples include phthalimide group or maleimide group.

As the lower alkanoyl group, straight- or branched-chain alkanoyl groups having 1 to 6 carbon atoms, preferably 1 to 4 carbon atoms may be used. For example, formyl group, acetyl group, propanoyl group, butyroyl group, or trimethylacetyl group may preferably be used. As the halogenated lower alkanoyl group, those may be used include the aforementioned alkanoyl group substituted with one or more halogen atoms which may be the same or different. As the halogen atom, any one of a fluorine atom, a chlorine atom, a bromine atom, or an iodine atom may be used. Preferred examples include fluoroacetyl group, difluoroacetyl group, trifluoroacetyl group, chloroacetyl group, dichloroacetyl group, and trichloroacetyl group.

As aryl groups that constitute the arylcarbonyl group, aryloxycarbonyl group, aralkyloxycarbonyl group, or aralkyl group, substituted or non-substituted aryl groups having 6 to 10 carbon atoms, e.g., phenyl group, p-methoxyphenyl group, p-chlorophenyl group, or naphthyl group, may be used. Benzoyl group or the like is preferable as the arylcarbonyl group, and phenoxycarbonyl group or the like is preferred as the aryloxycarbonyl group. As the aralkyloxycarbonyl group, preferable examples include benzyloxycarbonyl group, p-methoxybenzyloxycarbonyl group or the like, and as the aralkyl group, preferable examples include benzyl group, p-methoxybenzyl group or the like. As the lower alkyloxycarbonyl group, preferable examples include methoxycarbonyl group, ethoxycarbonyl group, tert-butoxycarbonyl group or the like. Trimethylsilyl group or the like may be used as the alkylsilyl group.

Among them, compounds wherein $R^3$ is a lower alkyloxycarbonyl group and $R^4$ is a hydrogen atom are preferred, and compounds wherein $R^3$ is tert-butoxycarbonyl group and $R^4$ is a hydrogen atom are particularly preferred. Where the groups represented by $R^2$, $R^3$, and $R^4$ have one or more asymmetric carbon atoms, the asymmetric carbon atom(s) may have any configuration(s). In addition, among the compounds of the present invention represented by formula (II), where $R^2$ is a hydrogen atom, or the amino group exhibit basicity depending on the sorts of $R^3$ and $R^4$, the compounds (II) may form acid addition salts or base addition salts. As the acid addition salts or base addition salts mentioned above, the pharmacologicallyacceptable acid addition salts or alkali addition salts exemplified above may preferably be used.

The compounds (I) and (II) of the present invention can be prepared, for example, according to the method disclosed in the specification of the Japanese Patent Application No. (Hei) 6-215213/1994.

More specifically, according to the first embodiment of the method for preparation, the compounds represented by formula (I) can be prepared by reacting a 7-halogenoquinoline-3-carboxylic acid derivative represented by the following formula (III):

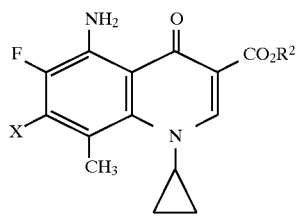

wherein R² represents a hydrogen atom or a lower alkyl group, and X represents a halogen atom, preferably a fluorine atom or a chlorine atom, and most preferably a fluorine atom, with a pyrrolidine derivative represented by the following formula (IV):

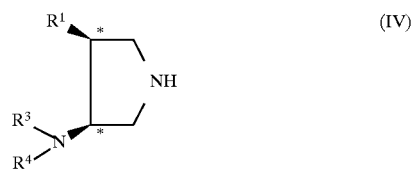

wherein each of $R^1$, $R^3$, $R^4$, and * has the same meaning as that defied above, in the presence or absence of a base in a solvent to obtain the compound (II), optionally followed by deblocking of $R^3$ and $R^4$ and ester hydrolysis of $R^2$.

As for the solvents used for the reaction of the compound represented by the general formula (III) with the compound represented by the general formula (IV), any solvents may be used so far that they, per se, are inert in the reaction, and do not inhibit the reaction. For example, alcoholic solvents such as methanol, ethanol, n-propanol, isopropanol, or n-butanol; aprotic polar solvents such as acetonitrile, N,N-dimethylformamide, N-methyl-2-pyrrolidone, dimethylsulfoxide, sulfolane, or hexamethylphosphoric triamide; aromatic hydrocarbonic solvents such as benzene or toluene; organic basic solvents such as pyridine, picoline, lutidine, or collidine; or mixed solvents thereof may be used.

Examples of the bases that are optionally used include, for example, triethylamine, N,N-diisopropylethylamine, 1,8-diazabicyclo[5.4.0]-7-undecene, 1,2,2,6,6-pentamethylpiperidine, 1,4-diazabicyclo [2.2.2]octane, sodium carbonate, potassium carbonate, sodium hydrogen carbonate, and potassium hydrogen carbonate. Where organic bases such as pyridine are used as solvents, addition of a base may sometimes be unnecessary since the solvents, per se, can work as bases. The reaction may be carried out at a temperature ranging from ice-cooling to refluxing temperature of a solvent.

Where $R^2$ is a lower alkyl group, the hydrolysis of the ester may be carried out according to a method that is known, per se, by using an acid or a base. Acids such as hydrochloric acid or sulfuric acid may be used for acidic hydrolysis, and alkalis such as sodium hydroxide or potassium hydroxide may be used for alkaline hydrolysis. These acids or alkalis may used as aqueous solutions, or alternatively, they may be used as solutions in organic solvents such as methanol, ethanol, n-butanol, sec-butanol, or tert-butanol; or as solutions in water-containing organic solvents. The reaction may be carried out at a temperature ranging from room temperature to refluxing temperature of a solvent.

The amino-deblocking reaction of $R^3$ and $R^4$ may be carried out by appropriate methods depending on the type of the protective group. For example, where $R^3$ is a lower alkanoyl group or a halogenated lower alkanoyl group, the compound (I) can be prepared by treating the compound (II) under a similar condition to that of the aforementioned hydrolysis reaction. Where ester-type groups such as tert-butoxycarbonyl group are used as $R^3$, deblocking reactions may be easily carried out by a treatment using an acid such as hydrochloric acid, hydrobromic acid, trifluoroacetic acid or the like without a solvent or in a solvent such as acetic acid, ethyl acetate, dioxane, water, methanol, ethanol, or a mixture thereof, optionally in the presence of a cation scavenger such as anisole or thioanisole. The reaction may be carried out at a temperature ranging from ice-cooling to refluxing temperature of a solvent.

According to the second embodiment of the method for preparation, the compound (I) can be prepared by reacting a boronic derivative represented by the following general formula (V):

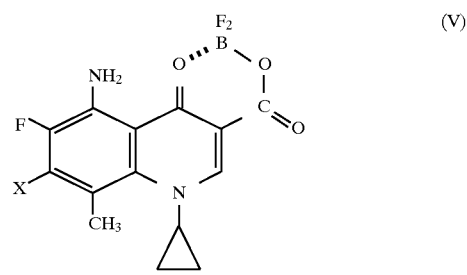

wherein X is the same as that defined above, with the pyrrolidine derivative represented by the aforementioned general formula (IV) in a solvent in the presence or absence of a base to prepare the compound (II), optionally followed by de-chelation of $R^2$ and deblocking of $R^3$ and $R^4$. The aforementioned de-chelation reactions may generally be carried out by a treatment with a protic polar solvent in the presence or absence of a base.

In the method for preparation according to the aforementioned second embodiment, as for the solvents used for the reaction of the compound represented by the general formula (V) with the compound represented by the general formula (IV), any solvents may be used so far that they, per se, are inert in the reaction, and do not inhibit the reaction. For example, alcoholic solvents such as methanol, ethanol, n-propanol, isopropanol, or n-butanol; aprotic polar solvents such as acetonitrile, N,N-dimethylformamide, N-methyl-2-pyrrolidone, dimethylsulfoxide, or hexamethylphosphoric triamide; aromatic hydrocarbonic solvents such as benzene or toluene; organic basic solvents such as pyridine, picoline, lutidine, or collidine; halogenated hydrocarbonic solvents such as dichloromethane, 1,2-dichloroethane, or chloroform: or mixed solvents thereof may be used.

Examples of the bases that are optionally used include, for example, triethylamine, N,N-diisopropylethylamine, 1,8-diazabicyclo[5.4.0]-7-undecene, 1,2,2,6,6-pentamethylpiperidine, 1,4-diazabicyclo [2.2.2]octane, sodium carbonate, potassium carbonate, sodium hydrogen carbonate, and potassium hydrogen carbonate. Where organic bases such as pyridine are used as solvents, addition of a base may sometimes be unnecessary since the solvents, per se, can work as bases. The reaction may be carried out at a temperature ranging from ice-cooling to refluxing temperature of a solvent.

As the protic polar solvents used in the de-chelation reaction, for example, alcoholic solvents such as methanol, ethanol, n-propanol, isopropanol, or n-butanol; water: or mixed solvents thereof may be used. Mixed solvents may also be used in which these solvents are added with aprotic solvents such as acetonitrile, N,N-dimethylformamide, N-methyl-2-pyrrolidone, dimethylsulfoxide, hexamethylphosphoric triamide, benzene, toluene, pyridine, picoline, lutidine, collidine, dichloromethane, 1,2-dichloroethane, or chloroform.

Examples of the bases that are optionally used in the de-chelation reaction include, for example, triethylamine, N,N-diisopropylethylamine, 1,8-diazabicyclo-[5.4.0]-7-undecene, 1,2,2,6,6-pentamethylpiperidine, 1,4-diazabicyclo[2.2.2]octane, sodium carbonate, potassium carbonate, sodium hydrogen carbonate, and potassium hydrogen carbonate. The reaction may be carried out at a temperature ranging from ice-cooling to refluxing temperature of a solvent.

Among the compounds used as starting materials for these methods of preparation, the compounds (III) and (V) can be prepared, for example, according to the method shown in the scheme set out below. In the scheme, the compound (VII) is known, i.e., disclosed in the Japanese Patent Unexamined Publication (KOKAI) No.(Sho)62-215572/1987. The symbol "X" has the same meaning as that defined above, and the symbol "Y" represents a halogen atom.

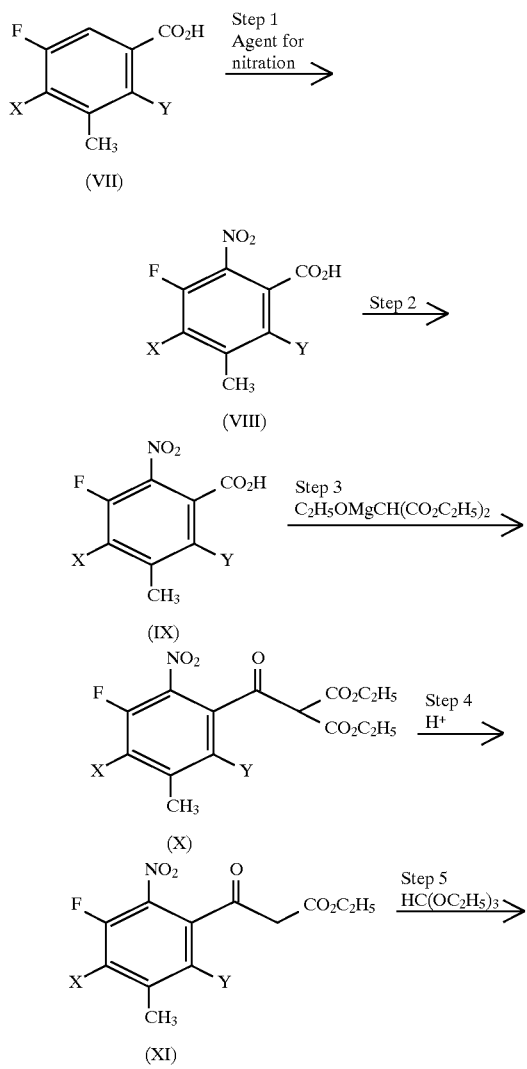

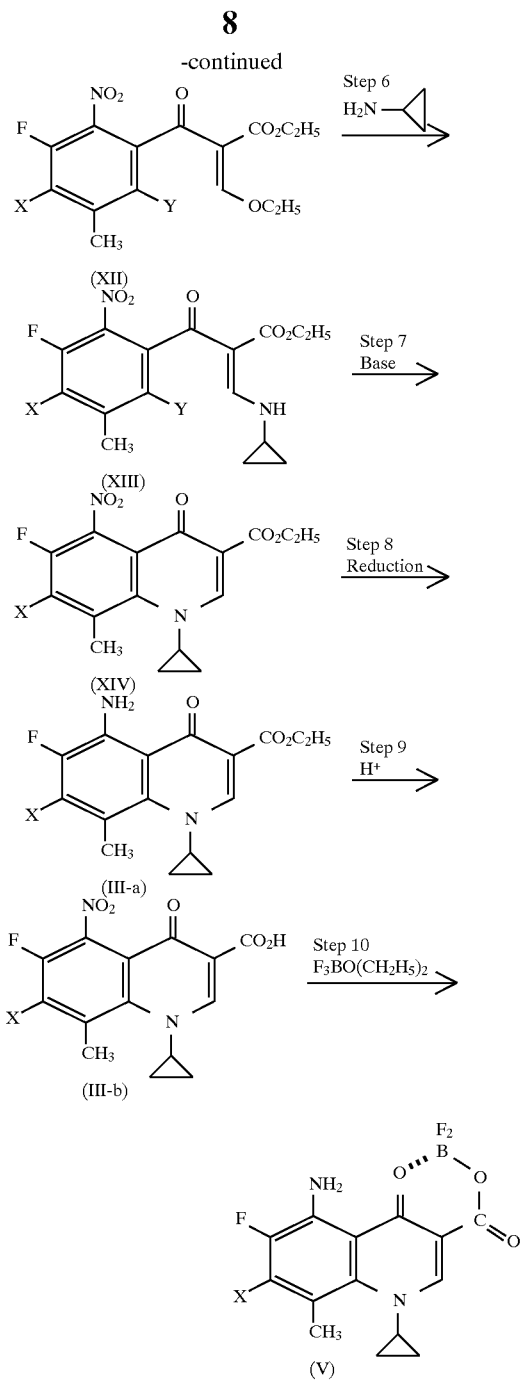

The reactions in the scheme will be explained. In the step 1 wherein 3-methyl-2,4,5-trihalogenobenzoic acid (VII) is subjected to nitration to obtain the compound (VIII), nitric acid, niter, ammonium nitrate or the like may be used as the agent for nitration. Sulfuric acid, acetic acid, acetic anhydride, trifluoroacetic anhydride, fuming nitric acid or the like may be used as a solvent. The resulting compound (VIII) is treated with a chlorinating agent such as thionyl chloride, oxalyl chloride or the like according to the step 2 to convert into the acid chloride (IX). Where a solvent is used, solvents such as chloroform, methylene chloride, 1,2-dichloroethane or the like may be used. The reaction may optionally be carried out in the presence of N,N-dimethylformamide.

The compound (X) is obtained by condensing diethyl ethoxy-magnesium-malonate, that is prepared from ethanol, diethyl malonate, and magnesium, with the above compound (IX) in a solvent such as benzene or toluene (step 3), and then the compound (X) is heated with water in the presence of an acid such as hydrochloric acid, sulfuric acid, p-toluenesulfonic acid or the like to obtain the compound (XI) by simultaneous hydrolysis and decarboxylation (step 4). After then, the compound (XI) is allowed to react with ethyl orthoformate in acetic anhydride to obtain the compound (XII) (step 5). This reaction may optionally be carried out in the presence of a Lewis acid such as zinc chloride.

The resulting compound (XII) is allowed to react with cyclopropylamine in a solvent to convert into the compound (XIII) (step 6). As the solvents, any solvents may be used so far that they, per se, are inert in the reaction and do not inhibit the reaction. For example, alcoholic solvents such as methanol or ethanol; halogenated hydrocarbonic solvents such as chloroform or 1,2-dichloroethane; aromatic hydrocarbonic solvents such as benzene or toluene; or aprotic polar solvents such as acetonitrile or N,N-dimethylformamide.

The compound (XIII) is then treated with a base in a solvent to obtain the compound (XIV) by a ring closure (step 7). Potassium carbonate, sodium hydride, potassium tert-butoxide or the like may be used as the base. As the solvents, ethereal solvents such as dioxane or tetrahydrofuran; or aprotic polar solvents such as acetonitrile, or N,N-dimethylformamide may be used. A catalyst may optionally be used in this reaction. For example, catalysts such as crown ethers, tetrabutylammonium bromide, benzyltriethylammonium bromide or the like may be employed.

The compound (III-a) can be obtained by subjecting the resulting compound (XIV) to catalytic hydrogenation using a catalyst such as Raney nickel, palladium carbon, platinum oxide or the like, or alternatively, to reduction under an acidic condition by using a metal such as iron, tin, zinc or the like (step 9). Acetic acid, water, methanol, ethanol, N,N-dimethylformamide or the like may be used as a solvent. Acids such as hydrochloric acid, acetic acid, hydrobromic acid or the like may be used for the reduction using a metal. The compound (III-b) can be obtained by hydrolyzing the compound (III-a) in a solvent such as water, acetic acid, alcohols, water-containing alcohols or the like under an acidic condition such as with hydrochloric acid, acetic acid, hydrobromic acid or the like. Then, the compound (V) can be obtained by reacting the compound (III-b) with boron trifluoride diethyl ether complex in a solvent such as ether, acetone, methylisobutylketone or the like. Each of the reactions has been explained along with the scheme. Further specific methods for preparation will be explained in Examples.

Among the pyrrolidine derivatives represented by the general formula (IV), compounds wherein $R^4$ is a hydrogen atom can be prepared according to the method shown in the scheme set out below. In the scheme, the compound (XV) is a known compound, i.e., disclosed in the Japanese Patent Publication for International Application (KOHYO) No. (Hei) 6-508136/1994. $R^1$ and $R^3$ are the same as those defined above, and the symbol "Z" represents a leaving group such as a halogen atom, triflate or the like.

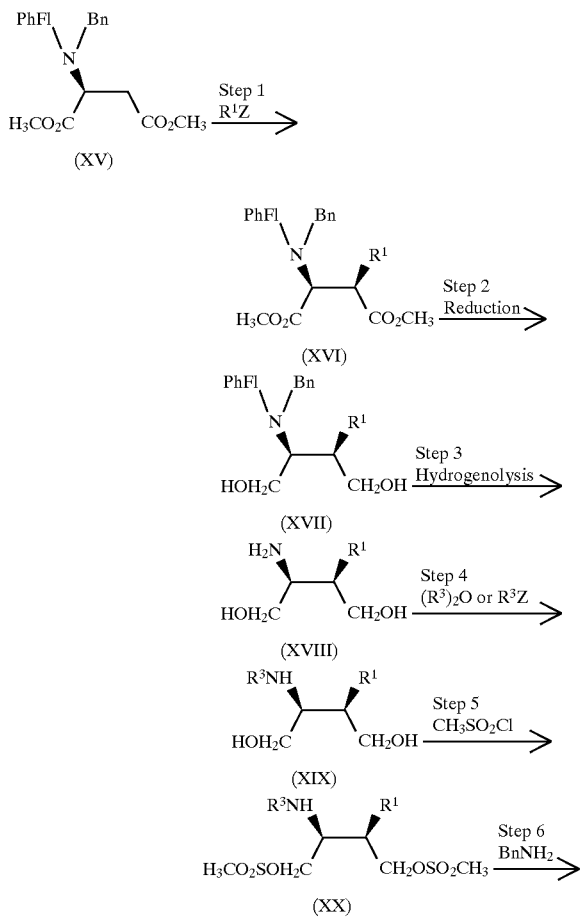

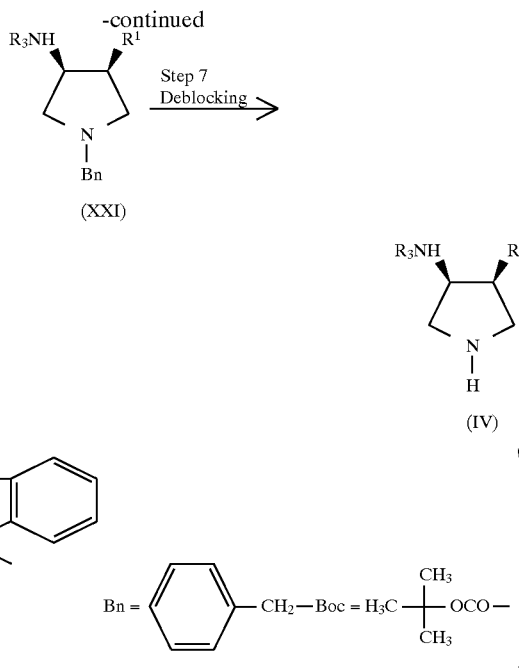

The reactions in the scheme will be explained. Step 1 comprises the step of treating the compound (XV) with an alkylating agent in a solvent in the presence of a base to obtain the compound (XVI). As the base, for example, lithium diisopropylamide (LDA), lithium bis(trimethylsilyl)amide or the like may preferably be used. As the solvent, for example, ethereal solvents such as ether, diisopropyl ether, tetrahydrofuran, 1,2-dimethoxyethane or the like may preferably be used. The reaction may be carried out at a temperature ranging from −75° C. to room temperature.

Step 2 comprises the step of treating the compound (XVI) with a reducing agent in a solvent to obtain the compound (XVII) whose amino group is protected. As the reducing agent, for example, lithium aluminum hydride, diisobutylaluminum hydride, bis(2-methoxyethoxy)aluminum hydride or the like may preferably be used. As the solvent, for example, ethereal solvents such as ether, diisopropyl ether, tetrahydrofuran or the like may preferably be used. The reaction may be carried out at a temperature ranging from −40° C. to a refluxing temperature of a solvent.

Step 3 comprises the step of hydrogenolyzing the compound (XVII) in a solvent in the presence of a catalyst to obtain the compound (XVIII) whose amino group is deblocked. As the catalyst, for example, catalysts for hydrogenation such as Raney nickel, palladium carbon, platinum oxide or the like may preferably be used. The sorts of the solvents are not particularly limited so far that they do not inhibit the reaction. For example, alcoholic solvents such as methanol, ethanol, propanol, or butanol; water-containing alcoholic solvents; aromatic hydrocarbonic solvents such as benzene, toluene, or xylene; aprotic polar solvents such as acetonitrile, N,N-dimethylformamide, or dimethylsulfoxide; ester-type solvents such as methyl acetate or ethyl acetate may be used. As the source of hydrogen, cyclohexadiene, formic acid, ammonium formate or the like as well as hydrogen gas may be used.

Step 4 comprises the step of treating the compound (XVIII) with $(R^3)_2O$ or $R^3Z$ in a solvent in the presence of absence of a base to obtain the compound (XIX) whose amino group is protected. As the base, for example, organic bases such as triethylamine, N,N-diisopropylethylamine, 1,8-diazabicyclo[5.4.0]-7-undecene, or pyridine; or inorganic bases such as sodium carbonate, potassium carbonate, sodium hydrogen carbonate, or potassium hydrogen carbonate may be used. As the solvent, for example, alcoholic solvents such as methanol, ethanol, propanol, or butanol; ethereal solvents such as ether, diisopropyl ether, tetrahydrofuran, or 1,2-dimethoxyethane; aprotic polar solvents such as acetonitrile, N,N-dimethylformamide, or dimethylsulfoxide; ester-type solvents such as methyl acetate or ethyl acetate; halogen-containing hydrocarbonic solvents such as methylene chloride, chloroform, or 1,2-dichloroethane may be used. The reaction may be carried out at a temperature ranging from ice-cooling to a refluxing temperature of a solvent.

Step 5 comprises the step of condensing the compound (XIX) with methanesulfonyl chloride in a solvent in the presence or absence of a base to obtain the compound (XX) in which each of the two hydroxyl groups is sulfonylated. As the base, for example, organic bases such as triethylamine, N,N-diisopropylethylamine, 1,8-diazabicyclo[5.4.0]-7-undecene, or pyridine; or inorganic bases such as sodium carbonate, potassium carbonate, sodium hydrogen carbonate, or potassium hydrogen carbonate may be used. The sorts of the solvents are not particularly limited so far that they do not inhibit the reaction. For example, aprotic polar solvents such as acetonitrile, N,N-dimethylformamide, or dimethylsulfoxide; ester-type solvents such as methyl acetate or ethyl acetate; halogen-containing hydrocarbonic solvents such as methylene chloride, chloroform, or 1,2-dichloroethane; aromatic hydrocarbonic solvents such as benzene, toluene, or xylene; ethereal solvents such as ether, diisopropyl ether, tetrahydrofuran, or 1,4-dioxane may be used. The reaction may be carried out at a temperature ranging from ice-cooling to a refluxing temperature of a solvent.

Step 6 comprises the step of reacting the compound (XX) with benzylamine in the presence or absence of a base in a solvent or without a solvent to prepare a (3S,4S)-3-amino-4-methyl (or ethyl)-pyrrolidine derivative (XXI) which is protected at the 1-position. As the base, for example, organic bases such as triethylamine, N,N-diisopropylethylamine, 1,8-diazabicyclo[5.4.0]-7-undecene, or pyridine; or inorganic bases such as sodium carbonate, potassium carbonate, sodium hydrogen carbonate, or potassium hydrogen carbonate may be used. The sorts of the solvents are not particularly limited so far that they do not inhibit the reaction. For example, aromatic hydrocarbonic solvents such as benzene, toluene, or xylene; aprotic polar solvents such as acetonitrile, N,N-dimethylformamide, or dimethylsulfoxide; ester-type solvents such as methyl acetate or ethyl acetate; halogen-containing hydrocarbonic solvents such as methylene chloride, chloroform, or 1,2-dichloroethane; ethereal solvents such as ether, tetrahydrofuran, 1,4-dioxane, or diisopropyl ether may be used. The reaction may be carried out at a temperature ranging from ice-cooling to 200° C.

Step 7 comprises the step of hydrogenolyzing the (3S,4S)-3-amino-4-methyl (or ethyl)-pyrrolidine derivative (XXI) which is protected at the 1-position in a solvent in the presence of a catalyst to prepare a (3S,4S)-3-amino-4-methyl (or ethyl)-pyrrolidine derivative (IV) whose 1-position is deblocked. As the catalyst, for example, catalysts for hydrogenation such as Raney nickel, palladium carbon, platinum oxide or the like may preferably be used. The sorts of the solvents are not particularly limited so far that they do not inhibit the reaction. For example, alcoholic solvents such as methanol, ethanol, propanol, or butanol; water-containing alcoholic solvents; aromatic hydrocarbonic solvents such as benzene, toluene, or xylene; aprotic polar solvents such as acetonitrile, N,N-dimethylformamide, or dimethylsulfoxide; ester-type solvents such as methyl acetate or ethyl acetate may be used. As the source of hydrogen, cyclohexadiene, formic acid, ammonium formate or the like as well as hydrogen gas may be used.

Each of the reactions has been explained along with the scheme. Further specific methods for preparation will be explained in Examples.

The medicament, which comprises, as an active ingredient, at least one substance selected from the group consisting of the aforementioned compound (I): 5-amino-7-((3S,4S)-3-amino-4-methyl-1-pyrrolidinyl)-1-cyclopropyl-6-fluoro-1,4-dihydro-8-methyl-4-oxoquinoline-3-carboxylic acid, 5-amino-7-((3S,4S)-3-amino-4-ethyl-1-pyrrolidinyl)-1-cyclopropyl-6-fluoro-1,4-dihydro-8-methyl-4-oxoquinoline-3-carboxylic acid, and pharmacologically acceptable salts thereof, is useful as an antibacterial agent. The antibacterial agents mentioned above may generally be administered for therapeutic and/or preventive treatments of infectious diseases of human or mammals as orally available preparations such as capsules, tablets, fine granules, granules, powders, syrups or the like, or alternatively, as injections, suppositories, eye drops, ophthalmic ointments, ear solutions, or topical preparations.

These preparations may be manufactured according to ordinary methods by using pharmacologically and pharmaceutically acceptable additives. For the manufactures of oral preparations and suppositories, pharmaceutical additives such as, for example, excipients such as lactose, D-mannitol, corn starch, or crystalline cellulose; disintegrators such as carboxymethylcellulose or carboxymethylcellulose calcium; binders such as hydroxypropylcellulose, hydroxypropylmethylcellulose, or polyvinylpyrrolidone; lubricants such as magnesium stearate or talc; coating materials such as hydroxypropylmethylcellulose, sucrose, or titanium oxide; plasticizer such as polyethyleneglycol; base materials such as polyethyleneglycol or hard fat may be used.

For the manufactures of injections, eye drops, or ear solutions, pharmaceutical additives such as solubilizers or solubilizing agents, which are ingredients for aqueous formulations or formulations to be dissolved before use, such as water for injection, physiological saline, or propyleneglycol; pH modifier such as inorganic or organic acids or bases; isotonicities such as sodium chloride, glucose, or glycerin; or stabilizers may be used. In addition, for the manufactures of ophthalmic ointments or topical preparations, pharmaceutical additives suitable as base materials for ointments, creams, or patches such as white soft paraffin, macrogol, glycerol, liquid paraffin, cotton sheet may be used.

Where the aforementioned antibacterial agent is administered for therapeutic or preventive treatment of a human infectious disease, an oral dose of about 10 to 1,000 mg, or parenteral dose of 1 to 500 mg per day for an adult may be administered once a day or several times as divided dosages. However, it is desirable that the dosage should be appropriately increased or decreased depending on the purpose of therapeutic or preventive treatment, focus of infection or the sort of pathogenic bacteria, the age of a patient, symptoms and the like.

EXAMPLE

The present invention will be explained more specifically by Examples. However, the scope of the present invention is not limited to these examples.

Example 1

Manufacture of the compound (I) of the present invention 2,4,5-Trifluoro-3-methyl-6-nitrobenzoic acid To a mixture of acids containing 370 ml of conc. sulfuric acid and 61.2 ml of 70% nitric acid, 36.6 g of 2,4,5-trifluoro-3-methylbenzoic acid was added portionwise at the inner temperature of 55°–70° C. with stirring, and then stirring was continued for 2 hours at room temperature. The reaction mixture was poured into ice and extracted with isopropyl ether. The extract was washed with brine, and then dried and concentrated to give 30.6 g of yellow crystals.

NMR spectrum $\delta(CD_3OD)$ ppm: 2.29 (3H, t, J=2 Hz)

Diethyl (2,4,5-trifluoro-3-methyl-6-nitrobenzoyl)malonate

A suspension containing 27.0 g of 2,4,5-trifluoro-3-methyl-6-nitrobenzoic acid, 19.5 ml of oxalyl chloride, 270 ml of methylene chloride, and a few drops of N,N-dimethylformamide was stirred at room temperature for 2 hours. The reaction mixture was concentrated under reduced pressure to give 2,4,5-trifluoro-3-methyl-6-nitrobenzoyl chloride. Separately, a few drops of carbon tetrachloride was added to a suspension of 3.08 g of magnesium in 6.4 ml of absolute ethanol, and then a solution of 19.2 ml of diethyl malonate in 12 ml of absolute ethanol was added dropwise to the suspension under heating at 50° C., and the mixture was stirred at the same temperature for 1.5 hours. The reaction mixture was concentrated under reduced pressure, and then, toluene was added to dissolve the residue and the solution was again concentrated. To a solution of the residue in 30 ml of toluene, a solution of 2,4,5-trifluoro-3-methyl-6-nitrobenzoyl chloride in 30 ml of toluene was added dropwise with stirring under ice cooling, and then stirring was continued for 2 hours at room temperature. The reaction mixture was added with 100 ml of 5% sulfuric acid, and was then extracted with diethyl ether. The extract was washed with brine, and then dried and concentrated to give 47.3 of brown oil.

NMR spectrum $\delta(CDCl_3)$ ppm: 1.12 (3H, t, J=7.5 Hz), 1.38 (3H, t, J=7.5 Hz), 2.33 (3H, t, J=2 Hz), 3.36, 14.18 (total 1H, each s), 4.07 (2H, q, J=7.5 Hz), 4.38 (2H, q, J=7.5 Hz)

Ethyl (2,4,5-trifluoro-3-methyl-6-nitrobenzoyl)acetate

A mixture of 45.3 g of diethyl (2,4,5-trifluoro-3-methyl-6-nitrobenzoyl)malonate, 30 mg of p-toluenesulfonic acid, and 120 ml of water was heated under reflux for 50 minutes. After cooling, the reaction mixture was extracted with diethyl ether, and the extract was washed with brine, and then dried and concentrated to give 34.2 g of brown oil.

NMR spectrum δ(CDCl$_3$) ppm: 1.26, 1.34 (total 3H, each t, J=7 Hz), 2.33, 2.35 (total 3H, each t, J=2.5 Hz), 3.91, 5.48, 12.34 (total 2H, each s), 4.20, 4.28 (total 2H, each q, J=7 Hz).

Ethyl 3-cyclopropylamino-2-(2,4,5-trifluoro-3-methyl-6-nitrobenzoyl)acrylate

A mixture of 31.9 g of ethyl (2,4,5-trifluoro-3-methyl-6-nitrobenzoyl)acetate, 26.2 ml of ethyl orthoformate and 23.8 ml of acetic anhydride was heated under reflux for 1 hour. The reaction mixture was concentrated under reduced pressure to give 46.2 g of ethyl 3-ethoxy-2-(2,4,5-trifluoro-3-methyl-6-nitrobenzoyl)acrylate as brown oil. To a solution of 45.4 g of the above compound in 328 ml of ethanol, 9.6 ml of cyclopropylamine was added dropwise with stirring under ice cooling, and then stirring was continued for 30 minutes at room temperature. The reaction mixture was concentrated under reduced pressure, and the residue was purified by column chromatography (silica gel, n-hexane-methylene chloride (1:1)) to give 28.8 g of yellow crystals. The crystals were recrystallized from isopropyl ether to give yellow needles, m.p. 115°–115.5° C.

| Analysis for C$_{16}$H$_{15}$F$_3$N$_2$O$_5$ | | | |
| --- | --- | --- | --- |
| Calculated % | C, 51.62 | H, 4.06 | N, 7.52 |
| Found % | C, 51.57 | H, 3.92 | N, 7.53 |

Ethyl 1-cyclopropyl-6,7-difluoro-1,4-dihydro-8-methyl-5-nitro-4-oxoquinoline-3-carboxylate To a solution of 27.1 g of ethyl 3-cyclopropylamino-2-(2,4,5-trifluoro-3-methyl-6-nitrobenzoyl)acrylate in 270 ml of dioxane, 3.2 g of 60% sodium hydride was added, and then stirring was continued for 1 hour at room temperature. Water (300 ml) was added to the reaction mixture, and then the crystals precipitated were collected by filtration to obtain 19.5 g of colorless crystals. The crystals were. recrystallized from N,N-dimethylformamide to colorless needles, m.p. 260°–263° C.

| Analysis for C$_{16}$H$_{14}$F$_2$N$_2$O$_5$ | | | |
| --- | --- | --- | --- |
| Calculated % | C, 54.55 | H, 4.01 | N, 7.95 |
| Found % | C, 54.51 | H, 4.00 | N, 7.90 |

Ethyl 5-amino-1-cyclopropyl-6,7-difluoro-1,4-dihydro-8-methyl-4-oxoquinoline-3-carboxylate A suspension containing 18.5 g of ethyl 1-cyclopropyl-6,7-difluoro-1,4-dihydro-8-methyl-5-nitro-4-oxoquinoline-3-carboxylate, 10 ml of Raney nickel, and 300 ml of acetic acid was hydrogenated at room temperature for 1.5 hours under atmospheric pressure. The catalyst was filtered off and the filtrate was concentrated. The resulting residue was added with 150 ml of 10% aqueous potassium carbonate, and then the mixture was extracted with methylene chloride. The organic layer was dried and concentrated to give 14.8 g of pale yellow crystals. The crystals were recrystallized from acetonitrile to give pale yellow needles, m.p. 182.5°–185.5° C.

| Analysis for C$_{16}$H$_{16}$F$_2$N$_2$O$_3$ | | | |
| --- | --- | --- | --- |
| Calculated % | C, 59.62 | H, 5.00 | N, 8.69 |
| Found % | C, 59.74 | H, 5.08 | N, 8.60 |

5-Amino-1-cyclopropyl-6,7-difluoro-1,4-dihydro-8-methyl-4-oxoquinoline-3-carboxlic acid A mixture of 14.8 g of ethyl 5-amino-1-cyclopropyl-6,7-difluoro-1,4-dihydro-8-methyl-4-oxoquinoline-3-carboxylate, 150 ml of 90% acetic acid, and 37.2 ml of conc. hydrochloric acid was heated under reflux for 2 hours. The crystals precipitated were collected by filtration and washed with water to give 11.8 g of yellow crystals. The crystals were recrystallized from N,N-dimethylformamide to give yellow crystals, m.p. 290.5° C. (decomp.).

| Analysis for C$_{14}$H$_{12}$F$_2$N$_2$O$_3$ | | | |
| --- | --- | --- | --- |
| Calculated % | C, 57.15 | H, 4.11 | N, 9.52 |
| Found % | C, 57.10 | H, 4.03 | N, 9.53 |

[5-Amino-1-cyclopropyl-6,7-difluoro-1,4-dihydro-8-methyl-4-oxoquinoline-3-carboxylate-O$^3$,O$^4$]difluoroboron (5-Amino-1-cycloprolpyl-6,7-difluoro-1,4-dihydro-8-methyl-4-oxoquinoline-3-carboxylic acid Bf$_2$ chelate)

A mixture of 5.00 g of 5-amino-1-cyclopropyl-6,7-difluoro-1,4-dihydro-8-methyl-4-oxoquinoline-3-carboxylic acid, 3.13 ml of boron trifluoride diethyletherate, and 75 ml of methyl isobutyl ketone was heated under reflux for 1 hour. After cooling, the crystals precipitated were collected by filtration and washed with diethyl ether to give 5.38 g of yellow crystals.

NMR spectrum δ(DMSO-d$_6$) ppm: 1.08–1.15 (2H, m), 1.21–1.30 (2H, m), 2.67 (3H, d, J=2.5 Hz), 4.52–4.59 (1H, m), 7.28 (2H, br-s), 9.10 (1H, s)

Dimethyl (2S,3R)-N-benzyl-3-methyl-N-(9-phenylfluoren-9-yl)aspartate

A solution of 1.66M of n-butyl lithium in 1966 ml of n-hexane was added dropwise with stirring to a solution of 608 ml of hexamethyldisilazane in 3.2 L of tetrahydrofuran at −10° C. under nitrogen atmosphere, and then stirring was continued at from −8° to 4° C. for 30 minutes. A solution of 942 g of dimethyl (2S)-N-benzyl-N-(9-phenylfluoren-9-yl) aspartate in 3.2 L of tetrahydrofuran was added dropwise to the above reaction solution while the temperature was kept in the range of from −28° to −23° C., and then the stirring was continued at from −26° to 24° C. for 30 minutes. After the mixture was cooled at from −65° to −64° C., the mixture was added dropwise with 143 ml of methyl iodide and then stirred at from −73° to −65° C. for 1.5 hours, and stirring was further continued for 1 hour at from −30° to −21° C. Saturated aqueous ammonium chloride (3.8 L) was added to the reaction mixture, and the mixture was stirred for 15 minutes under ice cooling and then layers were separated. The aqueous layer was extracted with ethyl acetate, and the extract was combined with the organic layer previously obtained and washed with brine. The extract was dried over sodium sulfate, and the solvent was evaporated under reduced pressure. The residue was washed with methanol to obtain 880 g of colorless crystals. The crystals were recrystallized from methanol to give the colorless plates, m.p. 153°–155° C.

| Analysis for C₃₃H₃₁NO₄ | | | |
|---|---|---|---|
| Calculated % | C, 78.39 | H, 6.18 | N, 2.77 |
| Found % | C, 78.41 | H, 6.15 | N, 2.75 |

Specific rotation $[\alpha]_D^{20}$ –344.5° (c=1, CHCl₃)
The following compound was obtained in a similar manner.
Dimethyl (2S,3R)-N-benzyl-3-ethyl-N-(9-phenylfluoren-9-yl)aspartate
Appearance: colorless plates (MeOH)
m.p.: 162.5°–163.5° C.

| Analysis for C₃₄H₃₃NO₄ | | | |
|---|---|---|---|
| Calculated % | C, 78.59 | H, 6.40 | N, 2.70 |
| Found % | C, 78.50 | H, 6.48 | N, 2.57 |

Specific rotation $[\alpha]_D^{20}$ –331.8° (c=1, CHCl₃)
(2S,3R-)-2-[N-Benzyl-N-(9-phenylfluoren-9-yl)]amino-3-methylbutane-1,4-diol A suspension of 63 g of lithium aluminum hydride in 3.0 L of anhydrous tetrahydrofuran was ice cooled, and a solution of 560 g of dimethyl (2S,3R)-N-benzyl-3-methyl-N-(9-phenylfluoren-9-yl)aspartate in 1.8 L of anhydrous tetrahydrofuran was added dropwise to the above suspension under nitrogen atmosphere. After the mixture was stirred at room temperature for 30 minutes, 300 ml of water and 110 ml of 15% aqueous sodium hydroxide were added successively to the mixture under ice cooling. Stirring was continued for 2 hours at room temperature, and then the insoluble substances were removed by filtration. The insoluble substances were washed with 1 L of tetrahydrofuran, and the filtrate and washings were combined and then concentrated under reduced pressure. The residue was dissolved in ethyl acetate, and the solution was dried over sodium sulfate, and then, the solvent was evaporated under reduced pressure to obtain 544 g of colorless viscous oil. This product was suitable for use in the next step without further purification. A part of the product was purified by column chromatography (silica gel, ethyl acetate:n-hexane=1:2) to give colorless viscous oil.

IR spectrum ν(liq) cm⁻¹: 3324 NMR spectrum δ(CDCl₃) ppm: 0.54 (3H, d, J=7 Hz), 1.50–1.60 (1H, m), 2.58–2.64 (1H, m), 2.84–2.93 (1H, m), 3.02–3.10 (1H, m), 3.12–3.19 (1H, m), 3.22–3.29 (1H, m), 4.18 (1H, d, J=15.5 Hz), 4.29 (1H, d, J=15.5 Hz), 7.17–7.75 (18H, m) Specific rotation $[\alpha]_D^{20}$ +106.7° (c=1, CHCl₃)

The following compound was obtained in a similar manner.
(2S,3R)-2-[N-Benzyl-N-(9-phenylfluoren-9-yl)]amino-3-ethylbutane-1,4-diol
Appearance: colorless oil
IR spectrum ν(liq) cm⁻¹: 3292 NMR spectrum δ(CDCl₃) ppm: 0.64 (3H, t, J=7.5 Hz), 0.81–1.02 (2H, m), 1.29–1.38 (1H, m), 1.81 (2H, br-s), 2.76–2.87 (2H, m), 3.08–3.17 (1H, m), 3.24–3.35 (2H, m), 4.09 (1H, d, J=15 Hz), 4.26 (1H, d, J=15 Hz), 7.16–7.77(18H, m) Specific rotation $[\alpha]_D^{20}$ + 158.90 (c=1, CHCl₃)
(2S,3R)-2-Amino-3-methylbutane-1,4-diol A mixture of 60 g of (2S,3R)-2-[N-benzyl-N-(9-phenylfluoren-9-yl)]amino-3-methylbutane-1,4-diol, 6.0 g of 20% palladium hydroxide on charcoal, and 500 ml of methanol was hydrogenated in an autoclave under 5 kgf/cm² hydrogen pressure at 40° C. for 2 hours. The catalyst was removed by filtration and the filtrate was concentrated under reduced pressure. The residue was added with isopropylalcohol and insoluble substances were removed by filtration. The filtrate was concentrated under reduced pressure to give 16.7 g of colorless viscous oil.

IR spectrum ν(liq) cm⁻¹: 3360 NMR spectrum δ(CDCl₃) ppm: 0.90 (3H, d, J=7.5 Hz), 1.65–1.76 (1H, m), 2.60–3.00 (5H, m), 3.50–3.61 (2H, m), 3.64–3.70 (2H, m)

The following compound was obtained in a similar manner.
(2S,3R)-2-Amino-3-ethylbutane-1,4-diol
Appearance: yellow oil
IR spectrum ν(liq) cm⁻¹: 3360 NMR spectrum δ(CDCl₃) ppm: 0.95 (3H, t, J=7.5 Hz), 1.29–1.49 (3H, m), 2.41 (4H, br-s), 2.95–3.05 (1H, m), 3.57–3.83 (4H, m)
(2S,3R)-2-(tert-Butoxycarbonyl)amino-3-methylbutane-1,4-diol A solution of 234 g of di-tert-butyldicarbonate in 140 ml of isopropylalcohol was added dropwise to a solution of 146 g of (2S,3R)-2-amino-3-methylbutane-1,4-diol in 500 ml of isopropylalcohol at room temperature with stirring. After stirring was continued at room temperature for 30 minutes, the solvent was evaporated under reduced pressure to give 260 g of pale yellow viscous oil. This product was suitable for use in the next step without further purification. A part of the product was purified by column chromatography (silica gel, methylene chloride:ethyl acetate=1:1) to give colorless viscous oil.

IR spectrum ν(liq) cm⁻¹: 3352, 1690 NMR spectrum δ(CDCl₃) ppm: 1.03 (3H, d, J=7 Hz), 1.45 (9H, s), 1.75–1.90 (1H, m), 2.72 (1H, br-s), 3.17 (1H, br-s), 3.42–3.80 (5H, m), 5.23 (1H, br-s) Specific rotation $[\alpha]_D^{20}$ –10.4° (c=1, CHCl₃)

The following compound was obtained in a similar manner.
(2S,3R)-2-(tert-Butoxycarbonyl)amino-3-ethylbutane-1,4-diol
Appearance: colorless oil.
IR spectrum ν(liq) cm⁻¹: 3384, 1692 NMR spectrum δ(CDCl₃) ppm: 0.98 (3H, t, J=7.5 Hz), 1.38–1.60 (3H, m), 1.45 (9H, s), 2.77 (1H, br-s), 2.84 (1H, br-s), 3.60–3.80 (5H, m), 5.28–5.35 (1H, m) Specific rotation $[\alpha]_D^{20}$ –0.4° (c=1, CHCl₃)
(2S,3R)-2-(tert-Butoxycarbonyl)amino-1,4-bis(methanesulfonyloxyy-3-methylbutane A solution of 249 g of (2S,3R)-2-(tert-butoxycarbonyl)amino-3-methylbutane-1,4-diol and 34 ml of triethylamine in 1,600 ml of methylene chloride was ice cooled, and the solution was added dropwise with methanesulfonyl chloride (174 ml) with stirring. After stirring was continued for 30 minutes at room temperature, the mixture was washed twice with water. The organic layer was dried over sodium sulfate and the solvent was evaporated under reduced pressure. The residue was washed with isopropyl ether to give 341 g of pale brown crystals.

IR spectrum ν(KBr) cm⁻¹: 3336, 1676 NMR spectrum δ(CDCl₃) ppm: 1.13 (3H, d, J=7 Hz), 1.45 (9H, s), 2.10–2.22 (1H, m), 3.04 (3H, s), 3.06 (3H, s), 3.81–3.93 (1H, m), 4.15–4.26 (2H, m), 4.26–4.40 (2H, m), 4.85 (1H, br-s) Specific rotation $[\alpha]_D^{20}$ –26.0° (c=1, CHCl₃)

The following compound was obtained in a similar manner.
(2S,3R)-2-(tert-Butoxycarbonyl)amino-1,4-bis(methanesulfonyloxy)-3-ethylbutane
Appearance: pale brown crystals
m.p.: 75.5°–76.5° C. (decomp.) IR spectrum ν(KBr) cm⁻¹: 3380, 1692 NMR spectrum δ(CHCl₃) ppm: 1.01 (3H, t, J=7.5 Hz), 1.38–1.68 (2H, m), 1.45 (9H,s), 1.90–2.00 (1H, m), 3.047 (3H, s), 3.053 (3H, s), 4.00–4.09 (1H, m), 4.28–4.38 (4H, m), 4.80–4.91 (1H, m) Specific rotation $[\alpha]_D^{20}$ –11.1° (c=1, CHCl$_3$)

(3S,4S)-1-Benzyl-3-(tert-butoxycarbonyl)amino-4-methylpyrrolidine

Benzylamine (290 ml) was stirred at room temperature and then added portionwise with (2S,3R)-2-(tert-butoxycarbonyl)amino-1,4-bis(methanesulfonyloxy)-3-methylbutane (100 g). The mixture was stirred at room temperature for 24 hours, and then poured into 600 ml of ice-water and stirring was continued for 30 minutes. The crystals precipitated were collected by suction filtration to give 45.1 g of pale brown crystals. The crystals were recrystallized from isopropyl ether to give colorless needles, m.p. 100°–102° C.

Specific rotation $[\alpha]_D^{20}$ +31.10 (c=1, CHCl$_3$)

The following compound was obtained in a similar manner. (3S,4S)-1-Benzyl-3-(tert-butoxycarbonyl)amino-4-ethylpyrrolidine Appearance: colorless needles (n-Hexane)
m.p. :97°–98.5° C.

| Analysis for C$_{18}$H$_{28}$N$_2$O$_2$ | | | |
|---|---|---|---|
| Calculated % | C, 71.02 | H, 9.27 | N, 9.20 |
| Found % | C, 71.02 | H, 9.55 | N, 8.93 |

Specific rotation $[\alpha]_D^{20}$ +31.9° (c=1, CHCl$_3$)

(3S,4S)-3-(tert-Butoxycarbonyl)amino-4-methylpyrrolidine

A mixture of 60.0 g of (3S,4S)-1-benzyl-3-(tert-butoxycarbonyl)amino-4-methylpyrrolidine, 6.00 g of 5% palladium on charcoal, and 500 ml of methanol was hydrogenated in an autoclave under 5 kgf/cm$^2$ hydrogen pressure at 40° C. for 3 hours. The catalyst was removed by filtration, and then the filtrate was concentrated under reduced pressure. The product was recrystallized from n-hexane to give 38.0 g of colorless needles, m.p. 83°–85° C.

NMR spectrum δ(CDCl$_3$) ppm: 0.97 (3H, d, J=7 Hz), 1.45 (9H, s), 2.20–2.30 (1H, m), 2.44–2.53 (1H, m), 2.70 (1H, dd, J=11.5, 4.5 Hz), 3.15 (1H, dd, J=11, 7.5 Hz), 3.20–3.30 (1H, m), 4.05–4.20 (1H, m), 4.62 (1H, br-s)

| High resolution mass spectrum for C$_{10}$H$_{21}$N$_2$O$_2$ | |
|---|---|
| Calculated m/z: | 201.1603 |
| Found m/z: | 201.1601 |

Specific rotation $[\alpha]D^{20}$ +19.6° (c=1, CHCl$_3$)

The following compound was obtained in a similar manner.

(3S,4S)-3-(tert-Butoxycarbonyl)amino-4-ethylpyrrolidine

Appearance: pale yellow crystals
m.p.: 63.5°–65.5° C. IR spectrum ν(KBr) cm$^{-1}$: 1712 NMR spectrum δ(CDCl$_3$) ppm: 0.94 (3H, t, J=7.5 Hz), 1.20–1.33 (1H, m), 1.39–1.51 (1H, m), 1.44 (9H, s), 1.98–2.08 (1H, m), 2.49–2.57 (1H, m), 2.75–2.81 (1H, m), 3.10–3.24 (2H, m), 4.09–4.20 (1H, m), 4.68–4.79 (1H, m) Specific rotation: $[\alpha]_D^{20}$ +2.30 (c=1, CHCl$_3$)

5-Amino-7-[(3S,4S)-3-tert-butoxycarbonylamino-4-methyl-1-pyrrolidinyl]-1-cyclopropyl-6-fluoro-1,4-dihydro-8-methyl-4-oxoquinoline-3-carboxylic acid A mixture of 1.01 g of [5-amino-1-cyclopropyl-6,7-difluoro-1,4-dihydro-8-methyl-4-oxoquinoline-3-carboxylic acid-O$^3$,O$^4$]difluoroborate, 0.71 g of (3S,4S)-3-tert-butoxycarbonylamino-4-methylpyrrolidine, 0.51 ml of N,N-diisopropylethylamine, and 4.04 ml of dimethylsulfoxide was stirred at outer temperature of 30° C. for 64 hours. Water was added to the reaction mixture under ice cooling, and the mixture was extracted with methylene chloride. The methylene chloride layer was washed successively with water and brine, and then dried and concentrated under reduced pressure. The resulting residue was purified by column chromatography (silica gel, methylene chloride: methanol= 100:1), and crystals obtained were washed with diethyl ether to give 0.58 g of yellowish orange crystals. A mixture of 0.58 g of the crystals obtained, 0.58 ml of triethylamine, 11.6 ml of methanol, and 5.8 ml of 1,2-dichloroethane was heated under reflux for 3 hours. The reaction mixture was concentrated under reduced pressure, and then, the residue was added with water and crystals precipitated were collected by filtration. The crystals were washed with water to give 0.52 g of yellow crystals. The crystals were recrystallized from acetone-diisopropyl ether to give yellow crystals, m.p. 178.5°–180° C.

| Analysis for C$_{24}$H$_{31}$FN$_4$O$_5$ | | | |
|---|---|---|---|
| Calculated % | C, 60.75 | H, 6.58 | N, 11.81 |
| Found % | C, 60.59 | H, 6.55 | N, 11.73 |

Specific rotation $[\alpha]_D^{20}$ –141.9° (c=0.1, CHCl$_3$)

5-Amino-7-[(3S,4S)-3-amino-4-methyl-1-pyrrolidinyl]-1-cyclopropyl-6-fluoro-1,4-dihydro-8-methyl-4-oxoquinoline-3-carboxylic acid 5-Amino-7-[(3S,4S)-3-tert-butoxycarbonylamino-4-methyl-1-pyrrolidinyl]-1-cyclopropyl-6-fluoro-1,4-dihydro-8-methyl-4-oxoquinoline-3-carboxylic acid (0.45 g) was added with stirring to 0.77 ml of conc. hydrochloric acid under ice cooling, and after stirring was continued for 3 minutes at room temperature, 0.77 ml of water was added to the mixture and stirring was further continued at room temperature for 10 minutes. The mixture was adjusted to pH 11 with 10% aqueous sodium hydroxide, and then to pH 8 with 10% hydrochloric acid and extracted with methylene chloride-methanol (9:1). The organic layer was washed with water and then dried, and concentrated under reduced pressure to obtain yellow crystals. The crystals were recrystallized from methylene chloride-diethyl ether to give 0.24 g of yellow crystals. The crystals were recrystallized from ethanol-diethyl ether to give yellow crystals, m.p. 212.5°–213.5° C.

| Analysis for C$_{19}$H$_{23}$FN$_4$O$_3$·¼H$_2$O | | | |
|---|---|---|---|
| Calculated % | C, 60.23 | H, 6.25 | N, 14.79 |
| Found % | C, 60.32 | H, 6.32 | N, 14.47 |

Specific rotation $[\alpha]_D^{20}$ –159.8° (c=0.1, DMF)

5-Amino-7-[(3S,4S-3-tert-butoxycarbonylamino-4-ethyl-1-pyrrolidinyl]-1-cyclopropyl-6-fluoro-1,4-dihydro-8-methyl-4-oxoquinoline-3-carboxylic acid A mixture of 2.00 g of 5-amino-1-cyclopropyl-6,7-difluoro-1,4-dihydro-8-methyl-4-oxoquinoline-3-carboxylic acid, 2.19 g of (3S,4S)-3-tert-butoxycarbonylamino-4-ethylpyrrolidine, 0.95 ml of triethylamine, and 8 ml of dimethylsulfoxide was heated with stirring at inner temperature of 94°–102° C. for 87 hours. The reaction mixture was poured into 40 ml of ice-water, and then the crystals precipitated were collected by filtration and washed with water to obtain 3.41 g of yellowish brown crystals. The product was purified by column chromatography (silica gel, methylene chloride:methanol=50:1) to give 2.01 g of yellow foamy product.

NMR spectrum δ(DMSO-d$_6$) ppm: 0.66–0.75 (1H, m), 0.80–0.85 (1H, m), 0.92 (3H, t, J=7.5 Hz), 1.03–1.19 (2H, m), 1.30–1.55 (2H, m), 1.41 (9H, s), 2.16–2.25 (1H, m), 2.32 (3H, s), 3.13–3.29 (1H, m), 3.41–3.52 (2H, m), 3.83–3.93 (1H, m), 4.10–4.29 (2H, m), 6.93–7.10 (3H, m), 8.60 (1H, s) Specific rotation $[\alpha]_D^{20}$ –213.1° (c=0.1, CHCl$_3$)

5-Amino-7-[(3S,4S)-3-amino-4-ethyl-1-pyrrolidinyl]-1-cyclopropyl-6-fluoro-1,4-dihydro-8-methyl-4-oxoquinoline-3-carboxylic acid Concentrated hydrochloric acid (2.9 ml) was stirred under ice cooling, and then added portionwise with 1.70 g of 5-amino-7-[(3S,4S)-3-tert-butoxycarbonylamino-4-ethyl-1-pyrrolidinyl]-1-cyclopropyl-6-fluoro-1,4-dihydro-8-methyl-4-oxoquinoline-3-carboxylic acid. The mixture was stirred at room temperature for 5 minutes, and then added with 2.9 ml of water and stirring was further continued for 10 minutes. The reaction mixture was added with 5 ml of methylene chloride and stirred, and then layers were separated and aqueous layer was washed twice with methylene chloride. The aqueous layer was added with 10% aqueous sodium hydroxide to adjust its pH to above 11. After stirring was continued for 20 minutes, the mixture was adjusted to pH 8 with 10% hydrochloric acid, and then crystals precipitated were collected by filtration and washed with water to obtain 1.09 g of yellow crystals. The crystals were recrystallized from methanol:water=4:1 to give 0.84 g of yellow crystals, m.p. 222.5°–224.5° C.

| Analysis for C$_{20}$H$_{25}$FN$_4$O$_3$·5/4H$_2$O | | | |
|---|---|---|---|
| Calculated % | C, 58.45 | H, 6.74 | N, 13.63 |
| Found % | C, 58.22 | H, 6.52 | N, 13.68 |

Specific rotation $[\alpha]_D^{20}$ –244.8° (c=0.1, 0.1N HCl)

Example 2

Test example

In the following test examples, 5-amino-7-((3S,4S)-3-amino-4-methyl-1-pyrrolidinyl)-1-cyclopropyl-6-fluoro-1,4-dihydro-8-methyl-4-oxoquinoline-3-carboxylic acid was used as the compound 1 of the present invention, and 5-amino-7-((3S,4S)-3-amino-4-ethyl-1-pyrrolidinyl)-1-cyclopropyl-6-fluoro-1,4-dihydro-8-methyl-4-oxoquinoline-3-carboxylic acid as the compound 2 of the present invention. Ciprofloxacin (The Merck Index 11th Edition, No.2315) was used as the reference compound A, and 5-amino-1-cyclopropyl-6-fluoro-1,4-dihydro-8-methyl-4-oxo-7-piperazinylquinoline-3-carboxylic acid (the Japanese Patent Unexamined Publication (KOKAI) No.(Sho) 62-215572/1987) as the reference compound B.

1. Antibacterial spectrum against standard strains and clinically isolated strains Antibacterial activities (minimum inhibitory concentration: MIC) were determined according to the standard method of the Japan Society of Chemotherapy (Chemotherapy (Tokyo), 29 (1), 76, 1981) by using standard strains and strains isolated from patients of infectious disease (clinically isolated strains) and applying $10^6$ viable cells per ml. Results are shown in Table 1-A and Table 1-B. The compound (I) of the present invention exhibited excellent antibacterial activities compared to the reference compound A and B, especially against clinically isolated strains. Names of the bacteria are as follows:

*Staphylococcus aureus* (*S. aureus*)

*Enterococcus faecalis* (*E. faecalis*)

*Escherichia coli* (*E. coli*)

*Klebsiella pneumoniae* (*K. pneumoniae*)

*Serratia marcescens* (*S. marcescens*)

*Enterobacter cloacae* (*E. cloacae*)

*Acinetobacter calcoaceticus* (*A. calcoaceticus*)

TABLE 1-A

| | | Antibacterial activities (standard strains, minimum inhibitory concentrations, μg/ml) | | | |
|---|---|---|---|---|---|
| Bacteria tested | Gram | Compound 1 | Compound 2 | Reference Compound A | Reference Compound B |
| *S. aureus* FDA 209P JC-1 | + | 0.006 | 0.006 | 0.20 | 0.10 |
| *E. coli* NIHJ JC-2 | − | 0.006 | 0.012 | 0.025 | 0.05 |
| *K. pneumoniae* PCI-602 | − | 0.0008 | ≦0.0015 | 0.012 | 0.006 |
| *S. marcescens* IAM 1184 | − | 0.05 | 0.10 | 0.10 | 0.20 |
| *E. colacae* 963 | − | 0.012 | 0.025 | 0.05 | 0.10 |

TABLE 1-B

| | | Antibacterial activities (clinically isolated strains, minimum inhibitory concentrations, μg/ml) | | | |
|---|---|---|---|---|---|
| Bacteria tested | Gram | Compound 1 | Compound 2 | Reference Compound A | Reference Compound B |
| *S. aureus* HPC527 | + | 0.006 | 0.006 | 0.39 | 0.10 |
| *S. aureus* HPC308 | + | 0.20 | 0.10 | 25 | 6.25 |
| *S. aureus* HPC292 | + | 0.78 | 0.78 | 50 | 25 |
| *E. faecalis* HPC984 | + | 0.05 | 0.05 | 0.39 | 0.39 |
| *E. faecalis* HPC948 | + | 0.10 | 0.20 | 3.13 | 6.25 |
| *E. faecalis* HPC975 | + | 0.78 | 0.78 | 50 | 12.5 |

TABLE 1-B-continued

Antibacterial activities (clinically isolated strains, minimum inhibitory concentrations, μg/ml)

| Bacteria tested | Gram | Compound 1 | Compound 2 | Reference Compound A | Reference Compound B |
|---|---|---|---|---|---|
| E. cloacae HNR1939 | − | 0.10 | 0.20 | 0.78 | 0.78 |
| E. cloacae HNR1946 | − | 0.10 | 0.20 | 0.78 | 0.78 |
| E. cloacae HNR1941 | − | 3.13 | 6.25 | 25 | 25 |
| A. calcoaceticus HNR916 | − | 0.006 | 0.012 | 0.39 | 0.10 |
| A. calcoaceticus HNR939 | − | 0.20 | 0.20 | 6.25 | 3.13 |
| A. calcoaceticus HNR904 | − | 1.56 | 3.13 | 100 | 50 |
| K. pneumoniae HNR858 | − | 0.10 | 0.20 | 0.78 | 0.78 |
| K. pneumoniae HNR869 | − | 0.78 | 1.56 | 3.13 | 6.25 |
| K. pneumoniae HNR828 | − | 3.13 | 3.13 | 12.5 | 12.5 |
| S. marcescens HNR1544 | − | 0.025 | 0.05 | 0.10 | 0.10 |
| S. marcescens HNR1792 | − | 1.56 | 1.56 | 6.25 | 6.25 |
| S. marcescens HNR1767 | − | 6.25 | 12.5 | 50 | 50 |

2. Chromosomal aberration test

The experiments were carried out using a Chinese hamster lung cell line (CHL cell). The test compounds prepared were added to cultured cells, and cultivation was continued for 6 hours at 37° C. in 5% $CO_2$. 2-(2-furyl)-3-(5-nitro-2-furyl) acrylamide was used as a positive control. After the cultivation for 6 hours, the cells were washed and added with fresh medium, and then cultivation was further continued for 18 hours. Colcemide solution was added to the culture 2 hours before the completion of the cultivation, and the chromosomal specimens were prepared after the cultivation was completed. Incidence rates of aberration cells were measured at the treatments with 100 μg/ml of the test compounds. As a result, the incidence rate of the aberration cells was less than 10% for each of the compound 1 of the present invention, the reference compound A, and the reference compound B.

3. Phototoxicity

Male Hartley guinea pigs were intravenously administered with test compounds at a dose of 10 mg/kg, and then immediately exposed to WVA on their backs for 90 minutes. Erythemas on the UV irradiated skin were observed 24 hours after the irradiation. The number of guinea pigs with erythemas was shown in Table 2. The compound 1 of the present invention induced no phototoxicity, whereas phototoxicities were observed in more than the half (three of five animals) as for the reference compound A.

4. The induction of convulsions

1) Intraperitoneal (i.p.) administration

Fasted five-week-old male ICR mice were orally administered with fenbufen at a dose of 100 mg/kg. After 30 minutes, the animals were intraperitoneally administered with the test compound at a dose of 100 mg/kg, and the absence or presence of induction of convulsions was observed. The number of mice with convulsions was shown in Table 2. The compound 1 of the present invention did not induce convulsions, whereas convulsions were observed in the half of the animals as for the reference compound A. In addition, although inducing actions of convulsions were not noticeable as for the reference compound B, all of the animals exhibited sedative symptoms that were considered as precursory symptoms of convulsions.

2) Intracerebroventricular (i.c.v.) administration

Male Wistar rats (weighing 180–220 g) were anesthetized with sodium pentobarbital at 45 mg/kg, i.p., and then the head of the rat was fixed in a stereotaxic apparatus. A stainless steel guide cannula for intracerebroventricular injection in 0.6 mm diameter was implanted as a guide cannula so as to be positioned at 1.5 mm above the left lateral cerebroventricle (A:6.2,R:1.0,H:+1.0) according to the brain atlas of De Groot (1959). The guide cannula was fixed by using a dental cement, and then closed with a stainless steel stylet in 0.3 mm diameter. Potassium penicillin G (10,000 units) were subcutaneously administered to prevent an infection. The rats were subjected to the experiments after recovery time for several days from the surgery.

For the measurement of the induction of convulsions, 50 mg/kg of fenbufen was intraperitoneally administered, and then the test compound was intracerebroventricularly administered after 30 minutes from the administration of fenbufen by means of a stainless steel cannula in 0.3 mm diameter that was connected with a polyethylene catheter and adjusted so as to be 1.5 mm longer than the guide cannula for an administration at an accurate position of cerebroventricle (H:+1.0). Absence or presence of appearance of convulsions was observed for at least 4 hours. After the completion of the above experiment, the administered positions were confirmed by intraventricularly injecting 10 μl of 1% Evans blue to each of the rats, and followed by sectioning the brains. The numbers of rats with induction of convulsions were shown in Table 2. The compound 1 of the present invention induced no convulsions, whereas convulsions were observed in all of the animals (each three animals) as for the reference compound A and B.

(Reference)

De Groot, J. (1959). The rat forebrain in stereotaxic coordinates. Ver. Kon. Ned. Acad. Wet., Natuurkunde 52: 1–40

TABLE 2

Photoxicity and induction of convulsions

| Compound tested | Photoxicity | Induction of convulsion i.p. | Induction of convulsion i.c.v. |
|---|---|---|---|
| Compound 1 | 0/5 | 0/6 | 0/6 |
| Reference Compound A | 3/5 | 3/6 | 3/3 |
| Reference Compound B | 0/5 | 0/6[1)] | 3/3 |

[1)]All of the animals exhibited sedative symptoms that were considered as precursory symptoms of convulsions

INDUSTRIAL APPLICABILITY

The compounds (I) of the present invention have excellent antibacterial activities, and induce no phototoxicity, chromosomal aberration, and induction of convulsion, and thus they are useful as antibacterial agents. The compounds (II) of the present invention are useful for efficient preparations of the aforementioned compounds (I).

What is claimed is:

1. A compound or a salt thereof represented by the following formula (I):

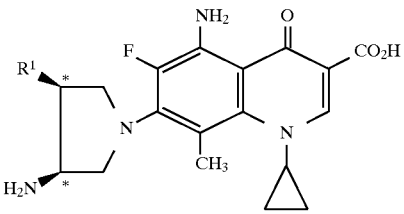

wherein asymmetric carbon atoms marked with asterisks are in the S-configurations, and $R^1$ represents methyl group or ethyl group.

2. 5-Amino-7-((3S,4S)-3-amino-4-methyl-1-pyrrolidinyl)-1-cyclopropyl-6-fluoro-1,4-dihydro-8-methyl-4-oxoquinoline-3-carboxylic acid or a salt thereof.

3. A compound represented by the following formula (II):

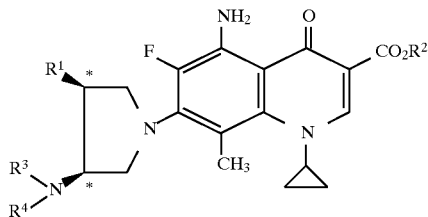

wherein the asymmetric carbon atoms marked with asterisks are in the S-configurations; $R^1$ represents methyl group or ethyl group; $R^2$ represents a hydrogen atom, a lower alkyl group, or $BF_2$ group; and $R^3$ and $R^4$ independently represent a hydrogen atom or an amino protective group; with the proviso that $R^2$, $R^3$, and $R^4$ are not simultaneously hydrogen atoms.

4. A pharmaceutical composition comprising a compound or a pharmacologically acceptable salt thereof represented by the following formula (I):

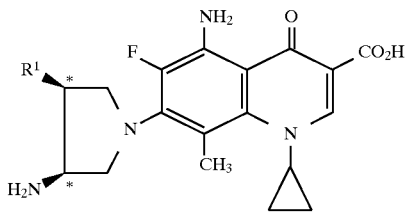

wherein asymmetric carbon atoms marked with asterisks are in the S-configurations, and $R^1$ represents methyl group or ethyl group.

5. An antibacterial method comprising administering a compound or a pharmacologically acceptable salt thereof represented by the following formula (I):

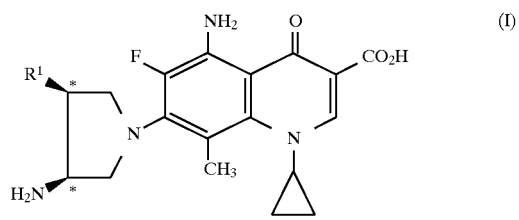

wherein asymmetric carbon atoms marked with asterisks are in the S-configurations, and $R^1$ represents methyl group or ethyl group.

6. An organic synthesis method comprising converting a compound represented by the following formula (I), wherein asymmetric carbon atoms marked with asterisks are in the S-configurations, and $R^1$ represents methyl group or ethyl group:

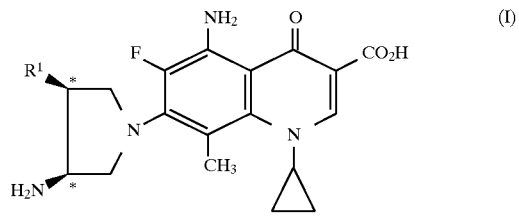

into a compound represented by the following formula (II):

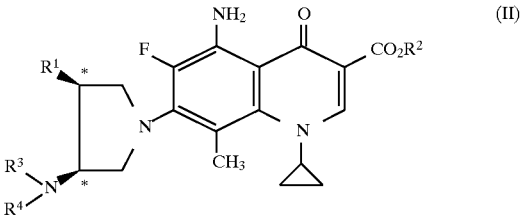

wherein asymmetric carbon atoms marked with asterisks are in the S-configurations; $R^1$ represents methyl group or ethyl group; $R^2$ represents a hydrogen atom, a lower alkyl group, or a $BF_2$ group; and $R^3$ and $R^4$ independently represent a hydrogen atom or an amino protective group; with the proviso that $R^2$, $R^3$, and $R^4$ are not simultaneously hydrogen atoms.

* * * * *